(12) United States Patent
Hasegawa et al.

(10) Patent No.: US 8,608,680 B2
(45) Date of Patent: Dec. 17, 2013

(54) DIALYSIS APPARATUS

(75) Inventors: Shinya Hasegawa, Makinohara (JP);
Kensaku Tanaka, Makinohara (JP)

(73) Assignee: Nikkiso Company Limited, Tokyo (JP)

( * ) Notice: Subject to any disclaimer, the term of this patent is extended or adjusted under 35 U.S.C. 154(b) by 0 days.

(21) Appl. No.: 13/565,123

(22) Filed: Aug. 2, 2012

(65) Prior Publication Data

US 2012/0302934 A1    Nov. 29, 2012

Related U.S. Application Data

(63) Continuation of application No. PCT/JP2011/052595, filed on Feb. 8, 2011.

(30) Foreign Application Priority Data

Feb. 9, 2010    (JP) ................................. 2010-026622

(51) Int. Cl.
*A61M 37/00*    (2006.01)
(52) U.S. Cl.
USPC ......................................... 604/6.11; 604/6.16
(58) Field of Classification Search
USPC .............................. 604/4.01–6.16; 422/44–48
See application file for complete search history.

(56) References Cited

U.S. PATENT DOCUMENTS 6,607,697 B1    8/2003 Muller

FOREIGN PATENT DOCUMENTS

| EP | 0930080 | 7/1999 | | |
|---|---|---|---|---|
| JP | 11-267197 | 10/1999 | | |
| JP | 2001-112863 | * 4/2001 | .............. | A61M 1/34 |
| JP | 2004-313522 | 11/2004 | | |

* cited by examiner

*Primary Examiner* — Philip R Wiest
(74) *Attorney, Agent, or Firm* — Harness, Dickey & Pierce, P.L.C.

(57) ABSTRACT

A dialysis apparatus has a dialysate infusing line. One end of the dialysate infusing line is connected to the dialysate introducing line or the dialysate discharging line. The other end is branched out at a branch point into two flow routes, respectively, a first branch end and a second branch end. The first branch end is connectable to the arterial blood circuit or the venous blood circuit. The second branch end is connectable to the tip end of the arterial blood circuit during the blood-returning process. A dialysate infusing pump is arranged on the dialysate infusing line at a connection-side of the dialysate infusing line relative to the dialysate introducing line or the dialysate discharging line from the branch point. The dialysate infusing pump supplies the dialysate of the dialysate introducing line or the dialysate discharging line to the first branch end and the second branch end.

6 Claims, 4 Drawing Sheets

DIALYSIS APPARATUS

CROSS-REFERENCE TO RELATED APPLICATIONS

This application is a continuation of International Application No. PCT/JP2011/052595, filed Feb. 8, 2011, which claims priority to Japanese Application No. 2010-026622, filed Feb. 9, 2010. The disclosures of the above applications are incorporated herein by reference.

FIELD

The present disclosure relates to a dialysis apparatus that enables a dialyzer (blood purification instrument) connected to a blood circuit to perform the dialysis.

BACKGROUND

In general, dialysis apparatus used for the hemodialysis treatment is provided with a dialysate introducing line and a dialysate discharging line, respectively, to supply the dialyzer, connected to the blood circuit, with dialysate and discharge dialysate containing blood waste materials produced by dialysis. The tips of the dialysate introducing line and the dialysate discharging line are connected, respectively, to a dialysate introducing port and a dialysate discharging port of the dialyzer.

In a blood purification instrument (dialyzer) applied to a hemodialysis filter (HDF) and using dialysate as the infusion solution (hereinafter referred to as "online HDF"), it is necessary to infuse the dialysate into the blood of a patient by an amount of ultrafiltration. Accordingly, a dialysis apparatus is proposed, for example in Japanese Laid-open Patent Publication No. 313522/2004. As shown, the dialysis apparatus has a blood circuit with a dialyzer 101 including an arterial blood circuit 102, arranged with a blood pump 104, and a venous blood circuit 103. A dialysate introducing line L1 introduce the dialysate, supplied by a pump 105, into the dialyzer 101. A dialysate discharging line L2 discharges the dialysate from the dialyzer 101. A bypass line L4 connects the dialysate introducing line L1 and the dialysate discharging line L2, not via the dialyzer 101. A dialysate infusing line L3 is coupled between the bypass line L4 and arterial blood circuit 102.

Such a dialysis apparatus of the online HDF is structured so that it ultrafiltrates a predetermined amount of water from blood during the hemodialysis treatment. It then replaces the ultrafiltrated water with dialysate while supplying the dialysate from the dialysate infusing line L3. A dialysate infusing pump 106 controls the flow rate through the dialysate infusing line L3 during the dialysate infusion. In FIG. 6, reference numerals 109 and 110 denote filters for filtering dialysate flowing through the dialysate introducing line L1. Reference character "V" denotes an electromagnetic valve. In addition, air trap chambers D1, D2 are arranged, respectively, on the arterial blood circuit 102 and the venous blood circuit 103.

The dialysis treatment is performed by connecting the base end of the dialysate infusing line L3 to one T-tube 107. The other tip end of the dialysate infusing line L3 is connected to the tip end of a tube "c" that extends from the air trap chamber D1 of the arterial blood circuit 102. The dialysate is infused from the air trap chamber D1 by an amount of water to be filtered (pre-dialysate infusion). The dialysate infusion (post-dialysate infusion) can also be performed by connecting the tip end of the dialysate infusing line L3 to the tip end of a tube extended from the air trap chamber D2.

The blood-return, after the dialysis treatment, can be performed by a dialysis apparatus as shown in FIG. 7. The tip end of the dialysate infusing line L3 is connected to the tip end (similarly to the priming, a connector after removal of an arterial puncture needle) of the arterial blood circuit 102. The dialysate is supplied from the pump 105 while keeping a puncture needle at the tip end of the venous blood circuit 103 punctured into a patient. This enables blood remaining in the blood circuits to be replaced with dialysate and the remaining blood to be returned into the body of a patient from the venous puncture needle. During this blood-returning process, it is also necessary to drive both the dialysate infusing pump 106 and the blood pump 104 to the normal rotational direction.

However, problems exist in the dialysis apparatus of the prior art. Usually, there is an error in the flow rate caused by general purpose pumps such as blood pump and dialysis pump relative to the set flow rate (discharging amount). Accordingly, it is believed that an excessive positive pressure would be caused in a flow route between the blood pump 104 and the dialysate infusing pump 106. Thus, the flow route would be broken when, for example, the discharging amount of the blood pump 104 is lower than that of the dialysate infusing pump 106 in the blood-returning process if the blood pump 104 is connected in series as shown in FIG. 7.

SUMMARY

It is, therefore, an object of the present disclosure to provide a dialysis apparatus that can prevent the generation of excessive positive pressure in the flow route between the blood pump and the dialysate infusing pump even though an error is caused in the flow rate of the blood pump and the dialysate infusing pump during the blood-returning process.

In order to achieve the present disclosure, a dialysis apparatus comprises a blood purification instrument that contains a blood purification membrane. The instrument includes a blood introducing port, a blood discharging port, a dialysate introducing port and a dialysate discharging port to perform the dialysis purification by contacting blood with dialysate through the blood purification membrane. An arterial blood circuit has a blood pump and a base end that is connected to the blood introducing port of the blood purification instrument. A venous blood circuit has a base end connected to the blood discharging port. A dialysate introducing line is connected to the dialysate introducing port of the blood purification instrument to introduce dialysate into the blood purification instrument. A dialysate discharging line is connected to the dialysate discharging port of the blood purification instrument to discharge dialysate from the blood purification instrument. A dialysate supplying device supplies prepared dialysate to the dialysate introducing line. The dialysis apparatus further comprises a dialysate infusing line. One end of the dialysate infusing line is connected to the dialysate introducing line or the dialysate discharging line. The other end is branched out at a branch point into two flow routes, respectively, a first branch end and a second branch end. The first branch end is able to be connected to the arterial blood circuit or the venous blood circuit. The second branch end is able to be connected to the tip end of the arterial blood circuit during the blood-returning process. A dialysate infusing pump is arranged on the dialysate infusing line at a connection-side of the dialysate infusing line relative to the dialysate introducing line or the dialysate discharging line from the branch point to supply the dialysate of the dialysate introducing line or the dialysate discharging line to the first branch end and the second branch end.

A valve device for cutting off or opening the supply of dialysate is arranged on the dialysate infusing line between the branch point and the second branch end.

The first branch end can be connected to an arterial air-trap chamber arranged on the arterial blood circuit or a venous air-trap chamber arranged on the venous blood circuit.

The dialysis apparatus further comprises a control device to synchronously control the blood pump and the dialysate infusing pump. Thus, the rotational speed of the dialysate infusing pump is higher than that of the blood pump by a predetermined ratio during the blood-returning process. The predetermined ratio is about 10%.

The control device controls the blood pump and the dialysate infusing pump. Thus, both the blood pump and the dialysate infusing pump are driven at the start of the blood-return. Only the dialysate infusing pump is driven after stopping the blood pump after the lapse of a predetermined time.

The dialysis apparatus comprises a dialysate infusing line. One end of the dialysate infusing line is connected to the dialysate introducing line or the dialysate discharging line. The other end is branched out at a branch point into two flow routes, respectively, a first branch end and a second branch end. The first branch end is able to be connected to the arterial blood circuit or the venous blood circuit. The second branch end is able to be connected to the tip end of the arterial blood circuit during the blood-returning process. Thus, it is possible, during the blood-returning process, to allow the dialysate to flow through both the flow route of the dialysate infusing line between the branch point and the second branch end and the flow route between the branch point and the first branch end. Accordingly, the dialysate can flow through the flow route between the branch point and the first branch end of the dialysate infusing line even when the flow rate (discharging amount) of the blood pump is lower than that of the dialysate infusing pump due to the error in flow rate of the blood pump and the dialysate infusing pump during the blood-returning process. Thus, the generation of excessive positive pressure in the flow route between the blood pump and the dialysate infusing pump can be prevented.

A valve device for cutting off or opening the supply of dialysate is arranged on the dialysate infusing line between the branch point and the second branch end. Thus, it is possible to surely prevent the dialysate from being discharged from the second branched end on the dialysate infusion line during dialysis treatment with the dialysate flow being cut off before the blood-return and opened during the blood-return by the valve device.

The first branch end can be connected to an arterial air-trap chamber arranged on the arterial blood circuit or a venous air-trap chamber arranged on the venous blood circuit. Thus, it is possible to perform the bubble removal on feeding the dialysate to the arterial blood circuit or the venous blood circuit during the dialysate infusion into the arterial blood circuit.

The dialysis apparatus further comprises a control device to synchronously control the blood pump and the dialysate infusing pump. Thus, the rotational speed of the dialysate infusing pump is higher than that of the blood pump by a predetermined ratio during the blood-returning process. Accordingly, it is possible to prevent back flow of the blood through the flow route between the branch point and the first branch end of the dialysate infusing line even though error would be caused in flow rate of the blood pump and the dialysate infusing pump during the blood-returning process.

The predetermined ratio is about 10%. Thus, it is possible to sufficiently absorb the error (about 10%) usually caused in general purpose pumps such as blood pumps and dialysate infusing pumps.

The control device controls the blood pump and the dialysate infusing pump. Both the blood pump and the dialysate infusing pump are driven at the start of the blood-return. Only the dialysate infusing pump is driven after stopping the blood pump after the lapse of a predetermined time. Thus, it is possible to reduce the consumption of dialysate during the blood-return and the time of blood-return.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

A preferable embodiment of the present disclosure will be hereinafter described with reference to the drawings.

Figure 1:
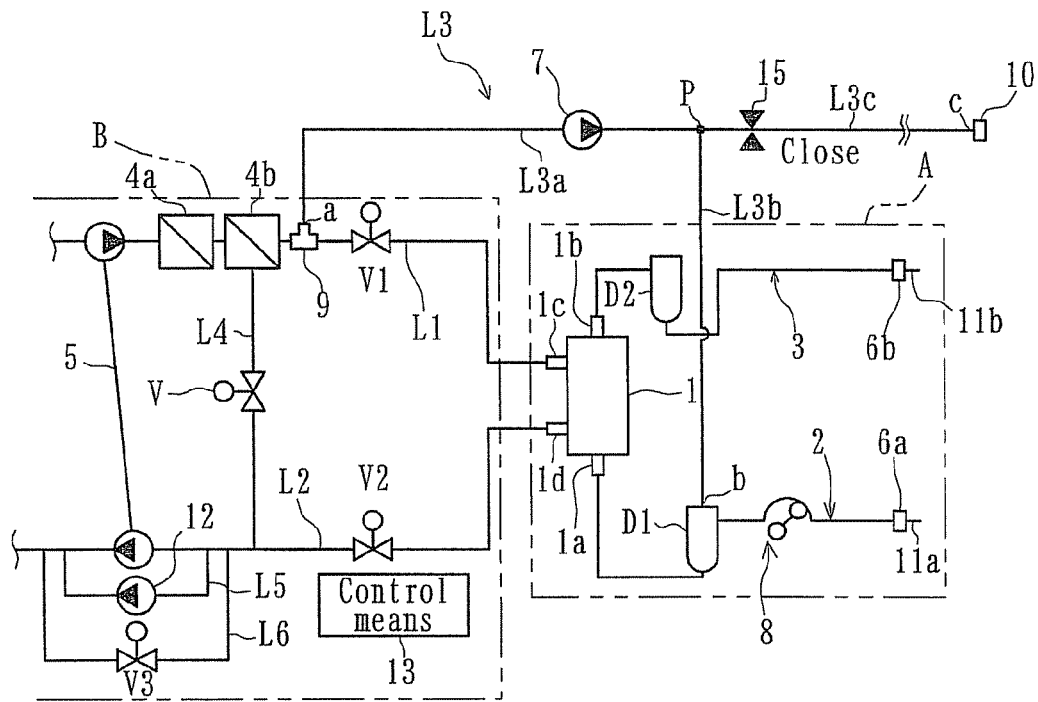
FIG. 1 is a schematic view of a dialysis apparatus of a first embodiment.

The dialysis apparatus of the present disclosure is applied to the hemodialysis (HD) and includes, as shown in FIG. 1, a blood circuit "A" and a dialysis apparatus main body "B". The blood circuit A includes an arterial blood circuit 2 and a venous blood circuit 3 connected to a dialyzer 1 as a blood purification instrument. The dialysis apparatus main body "B" includes a dialysate introducing line L1, a dialysate discharging line L2, and a dialysate infusing line L3 with a dialysate infusing pump 7.

The dialyzer 1 contains therein a blood purification membrane. The blood purification membrane is a hollow fiber membrane, however, a semi-permeable membrane and filtration membrane may be used. A blood introducing port 1a introduces blood to be dialyzed into the dialyzer. A blood discharging port 1b discharges dialyzed blood from the dialyzer. A dialysate introducing port 1c introduces the dialysate into the dialyzer. A dialysate discharging port 1d discharges the used dialysate in dialysis from the dialyzer. The dialyzer 1 can perform the dialysis for blood purification with contacting blood introduced via the blood introducing port 1a and with the dialysate through the hollow fiber membrane.

The arterial blood circuit 2 is mainly formed from a flexible tube adapted to be connected to the blood introducing port 1a of the dialyzer 1 at its base end. The arterial blood circuit 2 introduces blood collected from an artery of a patient into the hollow fiber membrane within the dialyzer 1. A connector 6a, for mounting an arterial puncture needle 11a, is secured on the tip end of the arterial blood circuit 2. An air trap chamber (arterial air trap chamber) D1 is arranged along the arterial blood circuit 2. In addition, a blood pump 8 of a peristaltic type, a pump adapted to discharge blood with the flexible tube being squeezed toward a predetermined direction from its outside, is arranged on the arterial blood circuit 2 at a position nearer to the tip end than the air trap chamber D1.

Similar to the arterial blood circuit 2, the venous blood circuit 3 is mainly formed from flexible tube and adapted to be connected at its base end to the blood discharging port 1b of the dialyzer 1. The venous blood circuit 3 discharges blood passed through flow routes in the hollow fiber membrane. A connector 6b, for mounting a venous puncture needle 11b, is secured on the tip end of the venous blood circuit 3. An air trap chamber (venous air trap chamber) D2 is arranged along the venous blood circuit 3.

The dialysate introducing line L1 and the dialysate discharging line L2 are connected, respectively, to the dialysate introducing port 1c and the dialysate discharging port 1d. The dialysate introduced into the dialyzer 1 from the dialysate introducing line L1 can be passed through the outside of the hollow fiber membrane and discharged through the dialysate discharging line L2. Electromagnetic valves V1 and V2 are arranged, respectively, along the dialysate introducing line L1 and the dialysate discharging line L2. In addition, a bypass line L4 is arranged between the dialysate introducing line L1 and the dialysate discharging line L2. The bypass line L4 connects the dialysate introducing line L1 and the dialysate discharging line but not through the dialyzer 1. An electromagnetic valve V is arranged on the bypass line L4.

A duplex pump (supply device) 5 is arranged within the dialysis apparatus main body "B". It is connected to both the dialysate introducing line L1 and the dialysate discharging line L2 in order to supply prepared dialysate to the dialysate introducing line L1. Bypass lines L5, L6, bypassing the duplex pump 5, are arranged on the dialysate discharging line L2. An ultrafiltration pump 12, for removing excessive water in blood of a patient, is arranged on the bypass line L5. An electromagnetic valve V3 is arranged on the bypass line L6. Reference numerals 4a, 4b denote filters to clean the dialysate. It is preferable to arrange at least one such filter, however, two or more filters may be arranged as shown in the present preferable embodiments.

In performing the hemodialysis treatment, first, the arterial puncture needle 11a and the venous puncture needle 11b are punctured into a body of a patient. Blood of a patient is extracorporeally circulated through the arterial blood circuit 2, the dialyzer 1 and the venous blood circuit 3 by driving the blood pump 8. The dialysate is introduced to the dialyzer 1 by driving the duplex pump 5. Thus, the blood of a patient is purified and the ultrafiltration is also performed by driving the ultrafiltration pump 12.

Figure 2:
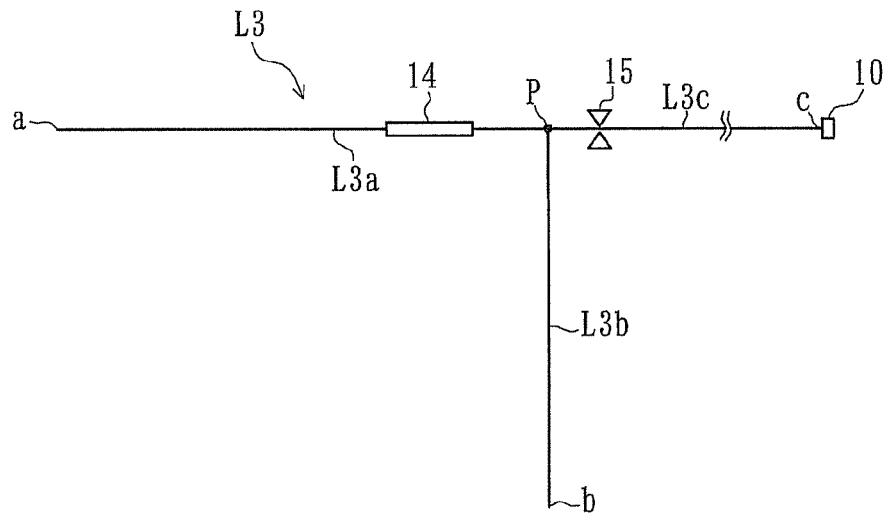
FIG. 2 is a schematic view of a dialysate infusing line of the dialysis apparatus of FIG. 1.
Figure 3:
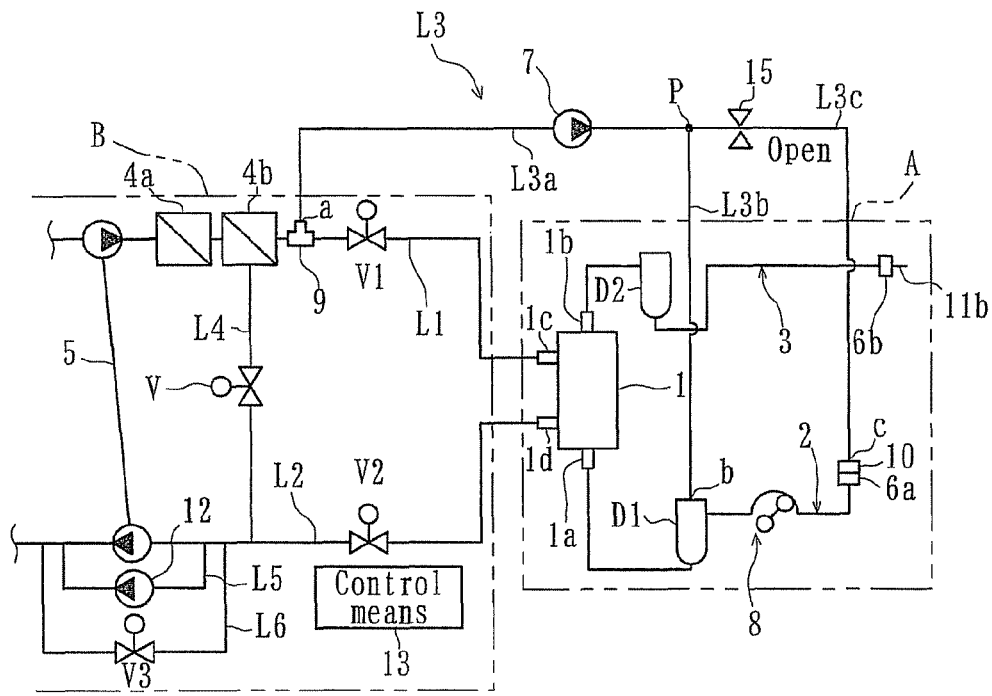
FIG. 3 is a schematic view of a connection of dialysate infusing line during the blood-return in the dialysis apparatus of FIG. 1.

The T-tube 9 is arranged along the dialysate introducing line L1, between the filter 4b and the electromagnetic valve V1. One end "a" of the dialysate infusing line L3 is connected to the T-tube 9. As shown in FIG. 2, the dialysate infusing line L3 is a flow route formed by a flexible tube, etc. It has one end "a" connected to the dialysate introducing line L1 via the T-tube and the other end is branched into a first branch end "b" and a second branch end "c". The first branch end "b" is connected to the air trap chamber (arterial air trap chamber) D1. The second branch end "c" can be connected to a tip end of the arterial blood circuit 2 during the blood-returning process. A reference numeral 14 denotes a tube portion to be squeezed by the dialysate infusing pump 7. The tube portion has a large diameter and is formed from a soft tube.

In the dialysate infusing line L3, it will be conveniently defined that a flow route from the one end "a" to the branch point "P" is a main flow route L3a. A flow route from the branch point "P" to the first branch end "b" is a first branch flow route L3b. A flow route from the branch point "P" to the second branch end "c" is a second branch flow route L3c. The tip end, the first branch end "b", of the first branch flow route L3 is previously connected to the air trap chamber D1. A connector 10, connectable to the connector 11a of the tip end of the arterial blood circuit 2, is mounted on the tip end, a second branch end "c", of the second branch flow route L3c.

The dialysate infusing pump 7 is a peristaltic pump arranged on the dialysate infusing line L3 at a connection-side of the dialysate infusing line L3, between the one end "a" and the branch point "P" of the main flow route L3a. The dialysate infusing pump 7 supplies the dialysate introducing line L1 to the first branch end "b", via the first branch flow route L3b, as well as to the second branch end "c", via the second branch flow route L3c. Thus, it is possible to perform the dialysate infusion (pre-dialysate infusion) during the hemodialysis treatment by driving the dialysate infusing pump 7 to supply the dialysate in the dialysate introducing line L1 to the arterial blood circuit 2, via the air trap chamber (arterial air trap chamber) D1.

In addition, a valve device 15, for cutting off and opening the supply of dialysate, is arranged on the dialysate infusing line L3 between the branch point P and the second branch end "c", along the second branch flow route L3c. Such a valve device 15 may be a clamp device or an electromagnetic valve. The clamp device enables cutting off and opening the supply of dialysate by manually clamping or unclamping of the flow route. The electromagnetic valve is capable of cutting off and opening the supply of the dialysate by clamping or unclamping the flow route.

In the present disclosure, the dialysis apparatus is structured so that the supply of dialysate is cut off during the hemodialysis treatment, including dialysate infusion, by closing the valve device 15 as shown in FIG. 1. Then, for performing the blood-return to a patient after completion of the hemodialysis treatment, the arterial puncture needle 11a is removed. The venous puncture needle 11b is kept punctured in a patient. The connector 10 of the second branch end "c", of the dialysate infusing line L3, is connected to the connector 6a of the tip end of the arterial blood circuit 2. During the blood-returning process, flow of the dialysate is maintained by opening the valve device 15.

The blood-return is carried out as follows. First, the piping of the dialysis apparatus main body "B" is separated from the blood flow route within the dialyzer 1. The electromagnetic valve "V" is opened while keeping the electromagnetic valves V1, V2 closed. This forms a flow route bypassing the dialyzer 1. The electromagnetic valve V3 of the bypass line L6 is also opened. Both the blood pump 8 and the dialysate infusing pump 7 are rotated toward their normal rotational direction under this condition. The dialysate in the dialysate introducing line L1 flows into the arterial blood circuit 2 via the main flow route L3a and the second branch flow route L3c of the dialysate infusing line L3. Thus, the blood-return can be performed by replacing the dialysate with blood. According to such a structure of the dialysis apparatus of the present disclosure, a portion of the dialysate can flow from the branch point "P" to the first branch end "b" through the first branch flow route L3b even if the flow rate caused by driving of the blood pump 8 is higher than that caused by driving of the dialysate infusing pump 7. Thus, the dialysate can flow into the arterial blood circuit 2 while bypassing the blood pump 8.

Also according to the present disclosure, the dialysis apparatus main body "B" is provided with a control device 13. The control device 13 includes a microcomputer etc. electrically connected to driving control device of the blood pump 8 and the dialysate infusing pump 7. Such a control device 13 controls the drive of the blood pump 8 and the dialysate infusing pump 7. The control device 13 can synchronously control the blood pump 8 and the dialysate infusing pump 7 so that the rotational speed of the dialysate infusing pump 7 is higher than that of the blood pump 8 by a predetermined ratio, about 10% in the preferable embodiment, during the blood-returning process. That is, since an error is caused in the actual flow rate of the dialysate infusing pump 7 and the blood pump 8 even if the driving speed of them is set, it is previously set in anticipation of the error so that the rotational speed of the dialysate infusing pump 7 is higher than that of the blood pump 8 by a predetermined ratio.

Thus, since the control device 13 can synchronously control the dialysate infusing pump 7 and the blood pump 8 so that the rotational speed of the dialysate infusing pump 7 is higher than that of the blood pump 8, by a predetermined ratio, it is possible to absorb the erroneous amount even if an error is caused in the flow rate of the dialysate infusing pump 7 and the blood pump 8. Accordingly, it is possible to prevent back flow, flow from the first branch end "b" to the branch point "P", of blood through the flow route between the branch point "P" and the first branch end "b" of the dialysate infusing line L3. This would be caused if the real flow rate of the blood pump 8 is higher than that of the dialysate infusing pump 7. Especially, according to the present disclosure, since the predetermined ratio is set at about 10%, it is possible to sufficiently absorb the error (about 10%) usually caused in general purpose pumps such as the blood pump 8 and the dialysate infusing pump 7.

In addition, the control device 13 of the present disclosure is so structured that it drives both the blood pump 8 and the dialysate infusing pump 7 at a commencement of the blood-return by the synchronous control as described above. The control device 13 stops the blood pump 8 after the lapse of a predetermined time and only drives the dialysate infusing pump 7. The phrase "after the lapse of a predetermined time" is a time after a duration where the flow route between the tip end of the arterial blood circuit 2 and the air trap chamber (arterial air trap chamber) D1 has been completely replaced by dialysate. It may be a time actually obtained from an experiment or a time theoretically obtained from a volume of the flow route and a flow rate of the dialysate. This makes it possible to reduce the usage amount of dialysate during the blood-return as well as the blood-returning time as compared to the case where the blood pump 8 and the dialysate infusing pump 7 are kept driven during the time from the start to the completion of the blood-returning process. According to the present disclosure, although the condition for stopping the blood pump 8 is a "time" required for completely replacing blood with dialysate, it is possible to directly detect the completion of the replacement by any concentration detecting device arranged in the blood circuit in place of measuring the "time".

According to the present disclosure, the dialysate infusing line L3 is structured so that one end "a" is connected to the dialysate introducing line L1 and the other end is branched out at a branch point "P" into two flow routes. The dialysate infusing line L3, respectively, has a first branch end "b" and a second branch end "c". The first branch end "b" is able to be connected to the arterial blood circuit 2. The second branch end "c" is able to be connected to the tip end of the arterial blood circuit 2 during the blood-returning process. Thus, it is possible, during the blood-returning process, to allow the dialysate to flow through both the flow route of the dialysate infusing line L3 between the branch point "P" and the second branch end "c" and the flow route between the branch point "P" and the first branch end "b".

Accordingly, the dialysate can flow through the flow route between the branch point "P" and the first branch end "b", of the dialysate infusing line L3, even when the flow rate (discharging amount) of the blood pump 8 is lower than that of the dialysate infusing pump 7 due to the error in flow rate of the blood pump 8 and the dialysate infusing pump 7 during the blood-returning process. Thus, the generation of excessive positive pressure in the flow route between the blood pump 8 and the dialysate infusing pump 7 can be prevented.

In addition, according to the present disclosure, a valve device 15 for cutting off and opening the supply of dialysate is arranged on the dialysate infusing line L3 between the branch point "P" and the second branch end "c". Thus, it is possible to surely prevent the dialysate from being discharged from the second branched end "c" of the dialysate infusion line during dialysis treatment. The dialysate flow is cut off before the blood-return and opened during the blood-return by the valve device 15.

Figure 4:
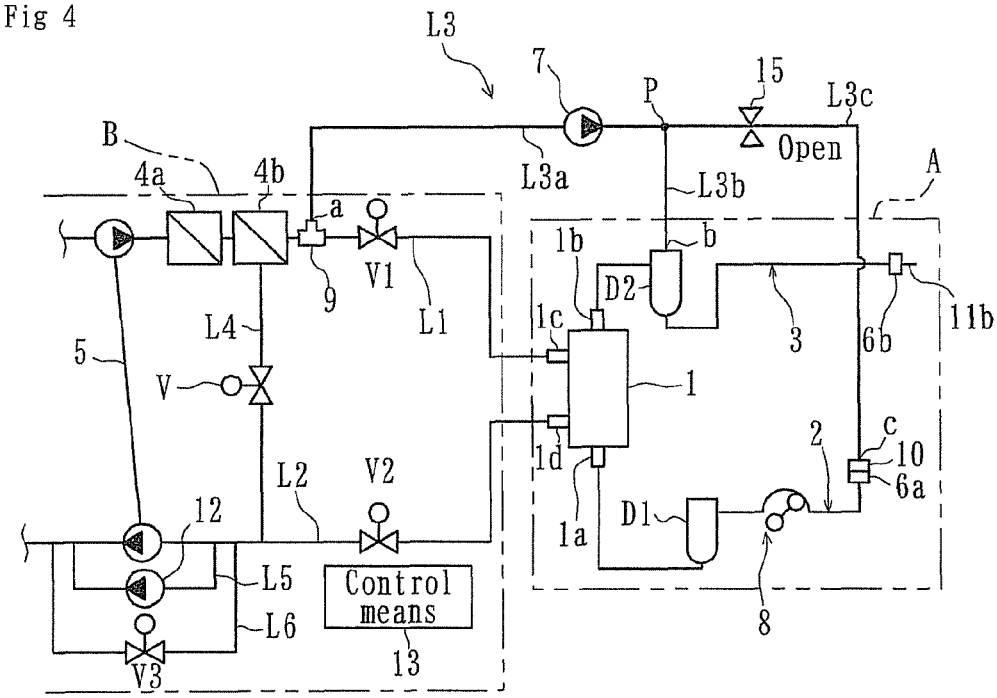
FIG. 4 is a schematic view of a connection of the dialysate infusing line during the blood-return in the dialysis apparatus of one modification of FIG. 1.
Figure 5:
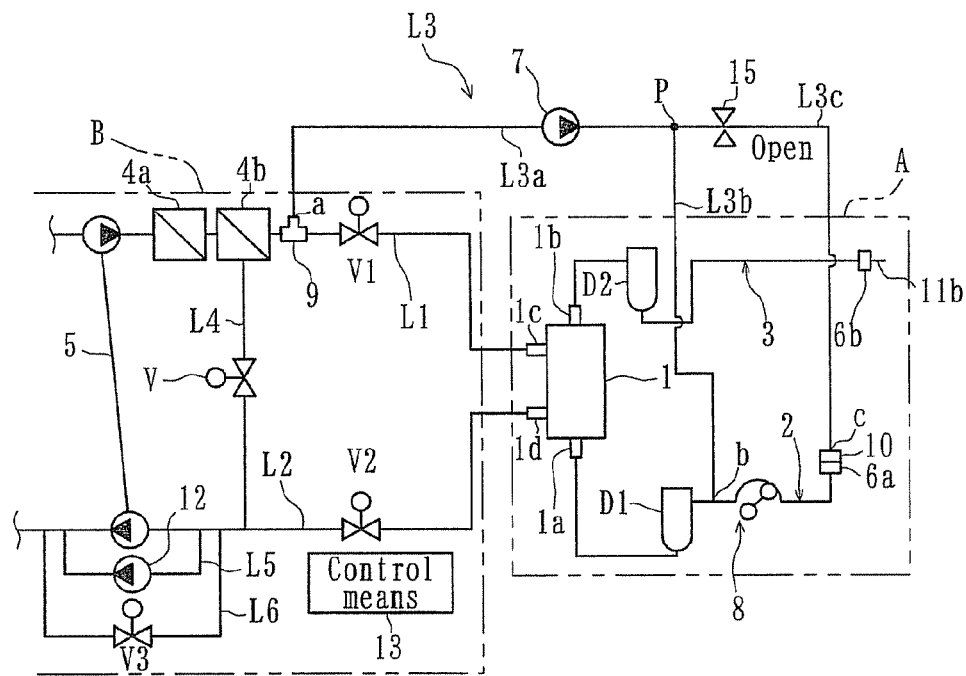
FIG. 5 is a schematic view of a connection of dialysate infusing line during the blood-return in the dialysis apparatus of another modification of FIG. 1.
Figure 6:
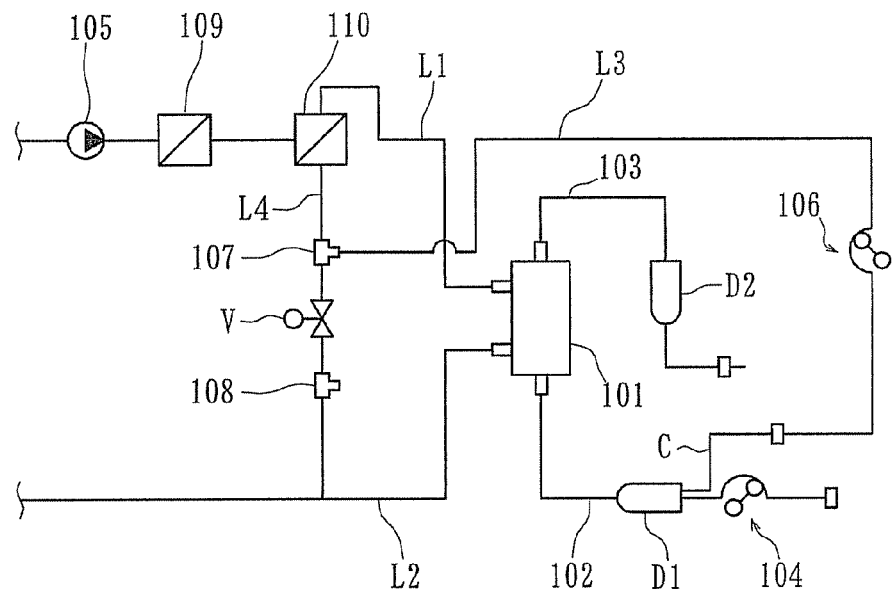
FIG. 6 is a schematic view of a prior art dialysis apparatus in a condition of hemodialysis treatment or dialysate infusion.
Figure 7:
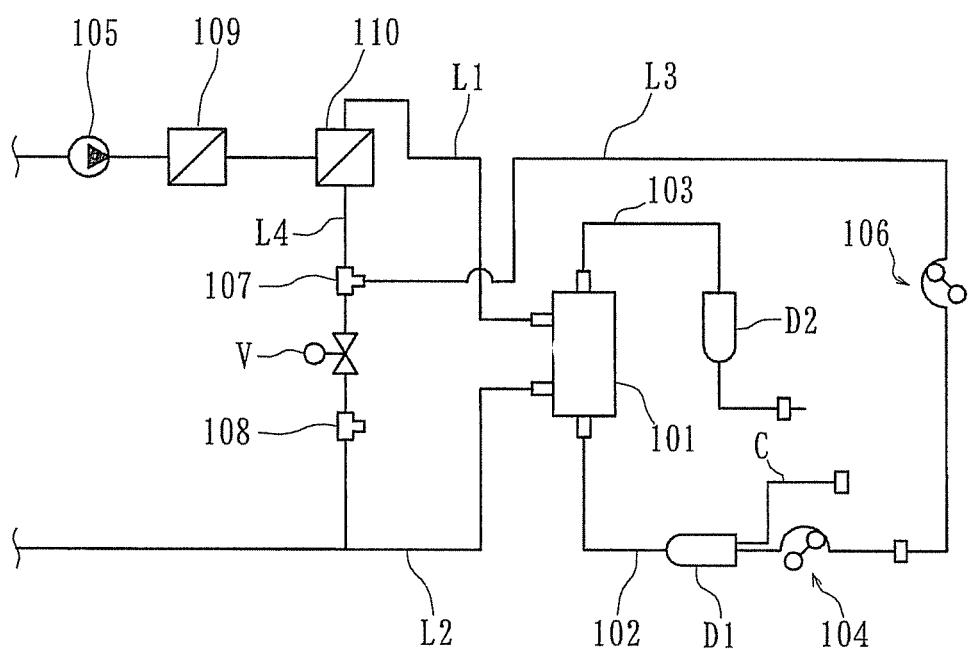
FIG. 7 is a schematic view of a prior art dialysis apparatus of FIG. 6 in a blood-return condition.

Further according to the present disclosure, the first branch end "b" can be connected to an arterial air-trap chamber (arterial air trap chamber) D1 arranged on the arterial blood circuit 2. Thus, it is possible to perform the bubble removal on feeding the dialysate to the arterial blood circuit 2 during the dialysate infusion into the arterial blood circuit 2. However, as shown in FIG. 4, it may be possible to perform the dialysate infusion (post-dialysate infusion) by connecting the first branch end "b" to the air trap chamber (venous air trap chamber) arranged along the venous blood circuit 3 and supplying the dialysate into the venous blood circuit 3 during the dialysate infusing process.

The preferable embodiments of the present disclosure have been described above. However, the present disclosure is not limited to these illustrated embodiments. For example, the dialysate infusing line may be a line where one end "a" is connected to the dialysate discharging line L2 or a line where the first branch end "b" is connected to the venous blood circuit 3. In addition, although the first branch end "b" is connected to the air trap chamber (arterial air trap chamber) D1 or to the air trap chamber (venous air trap chamber) D2, it may be connected to a flow route itself forming the arterial blood circuit 2 or it may be connected to a flow route itself forming the venous blood circuit 3.

The present disclosure can be applied to any other dialysis apparatus where functions other than those described in the present specification are added, if it is a dialysis apparatus, with a dialysate infusing line. One end of the dialysate infusing line is connected to the dialysate introducing line or the dialysate discharging line. The other end is branched out at a branch point into two flow routes, respectively, a first branch end and a second branch end. The first branch end is able to be connected to the arterial blood circuit or the venous blood circuit. The second branch end is able to be connected to the tip end of the arterial blood circuit during the blood-returning process. A dialysate infusing pump is arranged on the dialysate infusing line at a connection-side of the dialysate infusing line relative to the dialysate introducing line, or the dialysate discharging line from the branch point for supplying the dialysate of the dialysate introducing line or the dialysate discharging line to the first branch end and the second branch end.

The present disclosure has been described with reference to a preferred embodiment. Obviously, modifications and alternations will occur to those of ordinary skill in the art upon reading and understanding the preceding detailed description. It is intended that the present disclosure be construed to include all such alternations and modifications insofar as they come within the scope of the appended claims or their equivalents.

What is claimed is:

1. A dialysis apparatus comprising:
   a blood purification instrument including a blood purification membrane, a blood introducing port, a blood discharging port, a dialysate introducing port and a dialysate discharging port for performing the dialysis purification by contacting blood with dialysate through the blood purification membrane;
   an arterial blood circuit, with a blood pump, a tip end attachable with a patient via an arterial access needle and base end connected to the blood introducing port of the blood purification instrument;
   a venous blood circuit with a base end connected to the blood discharging port of the blood purification instrument;
   a dialysate introducing line connected to the dialysate introducing port of the blood purification instrument for introducing dialysate to the blood purification instrument;
   a dialysate discharging line connected to the dialysate discharging port of the blood purification instrument for discharging dialysate from the blood purification instrument;
   a dialysate supplying device for supplying prepared dialysate to the dialysate introducing line;
   a dialysate infusing line with one end connected to the dialysate introducing line or the dialysate discharging line, another end branched out at a branch point into two flow routes, respectively, a first branch end and a second branch end, the first branch end being able to be connected to the arterial blood circuit or the venous blood circuit, and the second branch end including a connector being able to be connected directly to the tip end of the arterial blood circuit, when the arterial access needle is not attached to the patient, during the blood-returning process; and
   a dialysate infusing pump arranged on the dialysate infusing line at a connection-side of the dialysate infusing line relative to the dialysate introducing line or the dialysate discharging line from the branch point for supplying the dialysate of the dialysate introducing line or the dialysate discharging line to the first branch end and the second branch end.

2. The dialysis apparatus of claim 1, wherein a valve device is arranged on the dialysate infusing line for cutting off or opening the supply of dialysate between the branch point and the second branch end.

3. The dialysis apparatus of claim 1, wherein the first branch end can be connected to an arterial air-trap chamber arranged on the arterial blood circuit or a venous air-trap chamber arranged on the venous blood circuit.

4. The dialysis apparatus of claim 1, wherein the dialysis apparatus further comprises a control device for synchronously controlling the blood pump and the dialysate infusing pump so that the rotational speed of the dialysate infusing pump is higher than that of the blood pump by a predetermined ratio during the blood-returning process into the arterial blood circuit.

5. The dialysis apparatus of claim 4, wherein the predetermined ratio is about 10%.

6. The dialysis apparatus of claim 4, wherein the control device controls the blood pump and the dialysate infusing pump so that both the blood pump and the dialysate infusing pump are driven at the start of the blood-return and only the dialysate infusing pump is driven after stopping the blood pump after the lapse of a predetermined time.

* * * * *